US00PP34984P2

(12) United States Plant Patent
Wilhoite et al.

(10) Patent No.: US PP34,984 P2
(45) Date of Patent: Feb. 14, 2023

(54) ***HOSTA* PLANT NAMED 'TWIN CITIES'**

(50) Latin Name: ***Hosta* hybrid**
Varietal Denomination: 'Twin Cities'

(71) Applicants: Chris Wilhoite, Indianapolis, IN (US); Cynthia Miller, Indianapolis, IN (US)

(72) Inventors: Chris Wilhoite, Indianapolis, IN (US); Cynthia Miller, Indianapolis, IN (US)

( * ) Notice: Subject to any disclaimer, the term of this patent is extended or adjusted under 35 U.S.C. 154(b) by 0 days.

(21) Appl. No.: 17/803,030

(22) Filed: Jan. 18, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 6/12
See application file for complete search history.

(56) References Cited

PUBLICATIONS

The Hosta Helper, "Hosta 'Paul's Glory'",downloaded from www.plantsgalore.com/hostas/cultivars/P/Hosta_Pauls_Glory.htm, pp. 1-8, downloaded Apr. 13, 2022.*
"Hosta 'Twin Cities'|Walters Gardens, Inc." (https://www.waltersgardens.com/variety.php?ID+HSTWC) downloaded Apr. 13, 2022, pp. 1-4.*
Chemically-Induced Polyploid Sports, downloaded from www.hostalists.org/hosta_list_chem.php, Apr. 26, 2019, p. 1.*
Zolock ("Polyploidy in Daylily and Hosta", 2003), pp. 1-10.*

* cited by examiner

*Primary Examiner* — Anne Marie Grunberg

(57) ABSTRACT

A new and distinct *Hosta* plant named 'Twin Cities' of large, upright spreading mound of dense, bullate, glaucous, ovate to round, variegated foliage with wide chartreuse margins, blue-green centers with a melding color zone between the center and the margins. The flowers are near light lavender, densely arranged in mostly upright scapes beginning to open just above the foliage in late June. 'Twin Cities' is useful in the landscape as a specimen or en masse.

5 Drawing Sheets

Botanical classification: *Hosta* hybrid.
Variety denomination: 'Twin Cities'.

STATEMENT REGARDING PRIOR DISCLOSURES UNDER 37 CFR 1.77(b)(6)

*Hosta* 'Twin Cities' was first introduced by the inventors as a brief non-enabling description and photograph on the website maintained by Walters Gardens, Inc. on Feb. 1, 2021. The first sale of the new plant was by Walters Gardens, Inc. on Jul. 5, 2021. Just prior to that, Walters Gardens, Inc. advertised the new plant in the "Walters Gardens 2021-2022 Catalog." Walters Gardens, Inc. obtained the new plant and all information about the new plant from us. No plants of *Hosta* 'Twin Cities' have been sold, in this country or anywhere in the world, nor has any disclosure of the new plant been made, more than one year prior the filing date of this application and all such plants sold within one year of this filing would be a U.S.C. § 102(b) exception.

BACKGROUND AND ORIGIN OF THE PLANT

The present invention relates to a new and distinct *Hosta* plant, *Hosta* 'Twin Cities' hereinafter also referred to as the new plant or by the cultivar name, 'Twin Cities'. *Hosta* 'Twin Cities' was a naturally-occurring sport mutation found in May of 2007 by the inventors, Chris Wilhoite and Cynthia Miller, on a portion of a clump of *Hosta* 'St Paul' (not patented) in a commercial perennial nursery in Indianapolis, Ind.

The new plant was initially isolated from the rest of the clump and has since been asexually propagated by division at the same nursery since 2012 and by sterile shoot tip plant tissue culture starting in about 2019 at a separate laboratory, with the resultant asexually propagated plants having retained all the same traits as the original plant. *Hosta* 'Twin Cities' is stable and reproduces true to type in successive generations of asexual reproduction.

There are over 7,300 registered and established *Hosta* cultivars accepted and recorded with The American *Hosta* Society, which is the International Cultivar Registration Authority for the genus *Hosta*. The new plant has not yet been registered with the International Cultivar Registration Authority. Several of these other registered and established cultivars have green leaf margins with chartreuse variegated leaf centers. The most similar *Hosta* cultivars known to the applicant are: 'Afterglow' U.S. Plant Pat. No. 26,755, 'American Gladiator' (not patented), 'Earth Angel' (not patented), 'Glory Hallelujah' (not patented), 'Jack of Diamonds' (not patented), 'Pauls Glory' (not patented), 'Terms of Endearment' U.S. Plant patent application Ser. No. 17/300,990, 'Tokudama Flavocircinalis' (not patented).

The sport parent, 'St Paul', has leaves with the yellow variegation in the center and a blue-green margin, the center portion is not as broad and the margin is wider in proportion. 'St Paul' is considered a ploidy chimera with the blue-green margin (L1 tunic layer) tetraploid and the yellow center (L2 tunic layer) being diploid. The new plant, 'Twin Cities', is diploid in both the L1 and L2 layers. 'Twin Cities' is more vigorous and the mature size significantly larger than 'St Paul'.

'Afterglow' has a less compact habit, the foliage is more ovate with more sharply acute apices and the flowers are paler lavender with more rounded tepals. 'American Gladiator' has a slightly smaller habit, the foliage is more bluish-green and the variegated margin is a narrower yellow. 'Earth Angel' has a larger habit and larger leaves that are more ovate and less rounded with a narrower lighter variegated yellow margin and the scapes are much taller. 'Glory Hallelujah' has a similar habit, but the variegated yellow margin is much narrower and the medium blue-green is much wider in proportion. 'Jack of Diamonds' has a smaller habit, with smaller leaves, the yellow variegated margins are narrower and the flowers are near-white to white. 'Paul's Glory' has an opposite, variegated, leaf pattern with the yellowish color in the middle and the bluish-green on the margin. 'Terms of Endearment' has a narrower, yellow, variegated margin and the flowers are near white with a blush of very pale purple. 'Tokudama Flavocircinalis' has a slower growth rate with flowers that are more white and the yellow variegated margin tends to be narrower.

Other *Hosta* cultivars may have variegated ovate leaf blades with bluish-green margins and chartreuse to yellow centers, or other individual traits similar to 'Twin Cities' but the new plant differs from the above-listed cultivars and all other hostas known to the applicant, by the combination of the following traits.

1. Habit is a large, upright, spreading mound of dense foliage;
2. Leaves are large-sized, lightly glaucous, ovate to round, thick textured, with acute apices and cordate base;
3. Leaves have a wide chartreuse margin and a blue-green center with heavy dimpling between the veins;
4. The transition between the margin and the center of the leaves is a melded effect;
5. Flowers are near light lavender and densely arranged on mostly upright scapes with the first flowers beginning to open just above the foliage;
6. Flowers are subtended by persistent, lanceolate, short, greenish, floral bracts.

BRIEF DESCRIPTION OF THE DRAWING

The photographs of the new plant demonstrate the overall appearance of the plant, including the unique traits. The colors are as accurate as reasonably possible with color reproductions. Ambient light spectrum, temperature, source and direction may cause the appearance of minor variation in color. The drawings show 'Twin Cities' plant in various growing conditions.

DETAILED BOTANICAL DESCRIPTION

Figure 1:
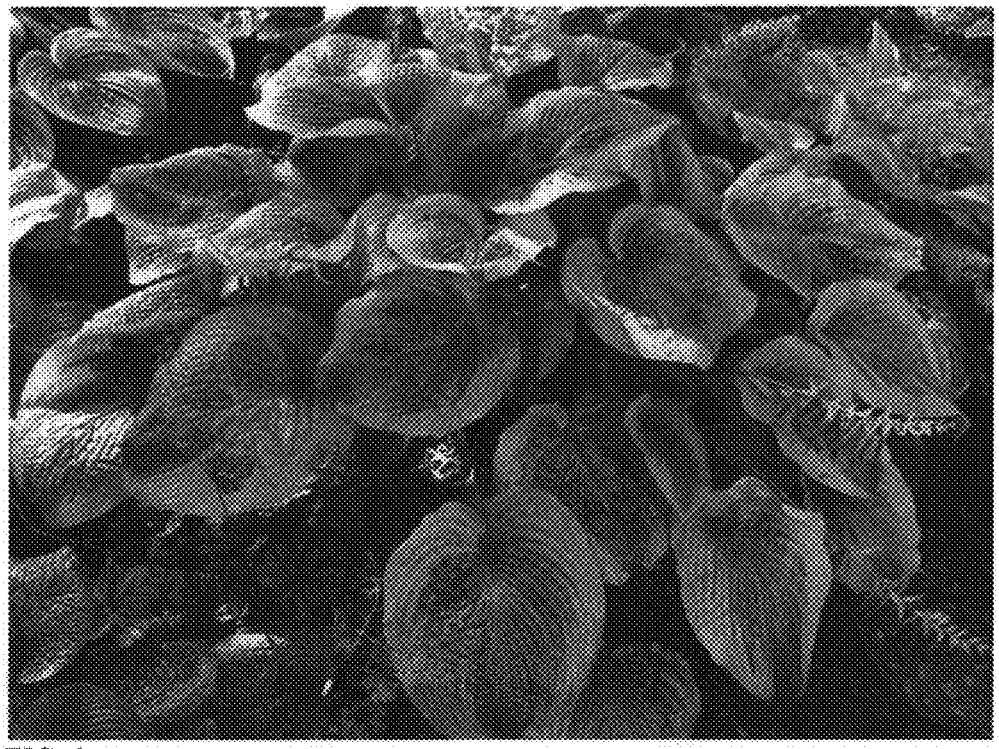
FIG. 1 shows a mature ten-year-old plant viewed from above in a display garden at a nursery in Indianapolis, Ind.
Figure 2:
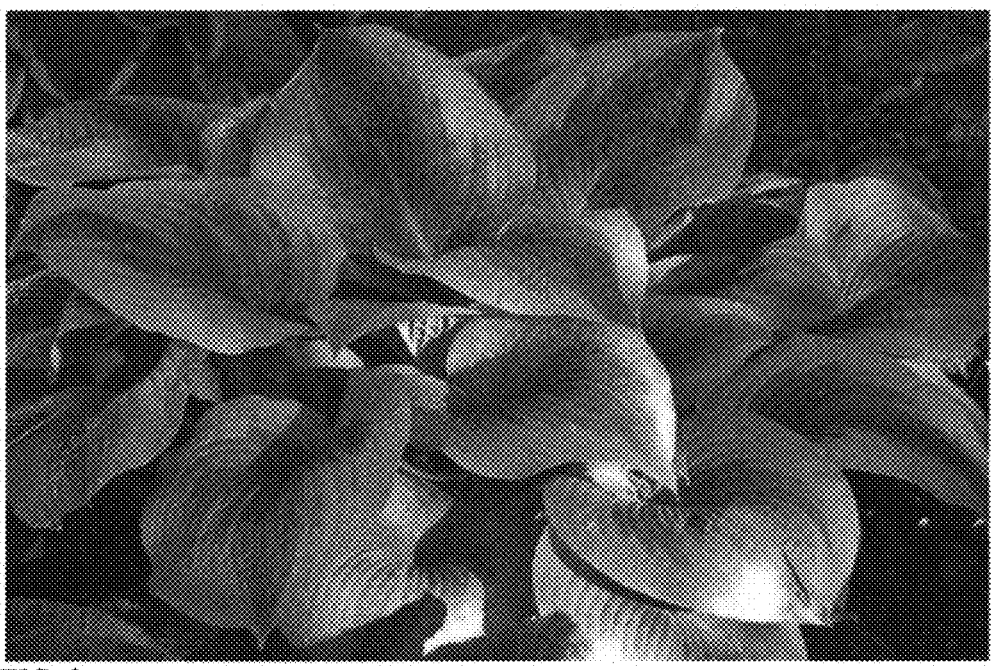
FIG. 2 shows a semi-mature plant prior to flowering in a display garden at a nursery in Indianapolis, Ind.
Figure 3:
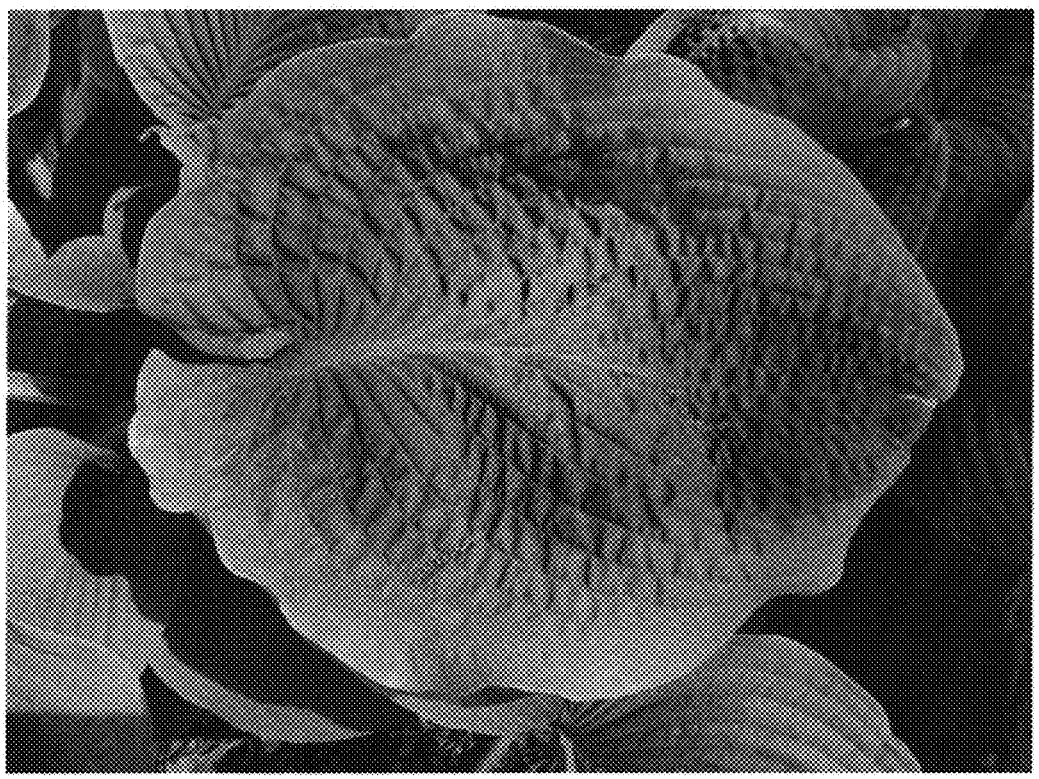
FIG. 3 shows a close-up of a mature leaf of the new plant prior to flowering.
Figure 4:
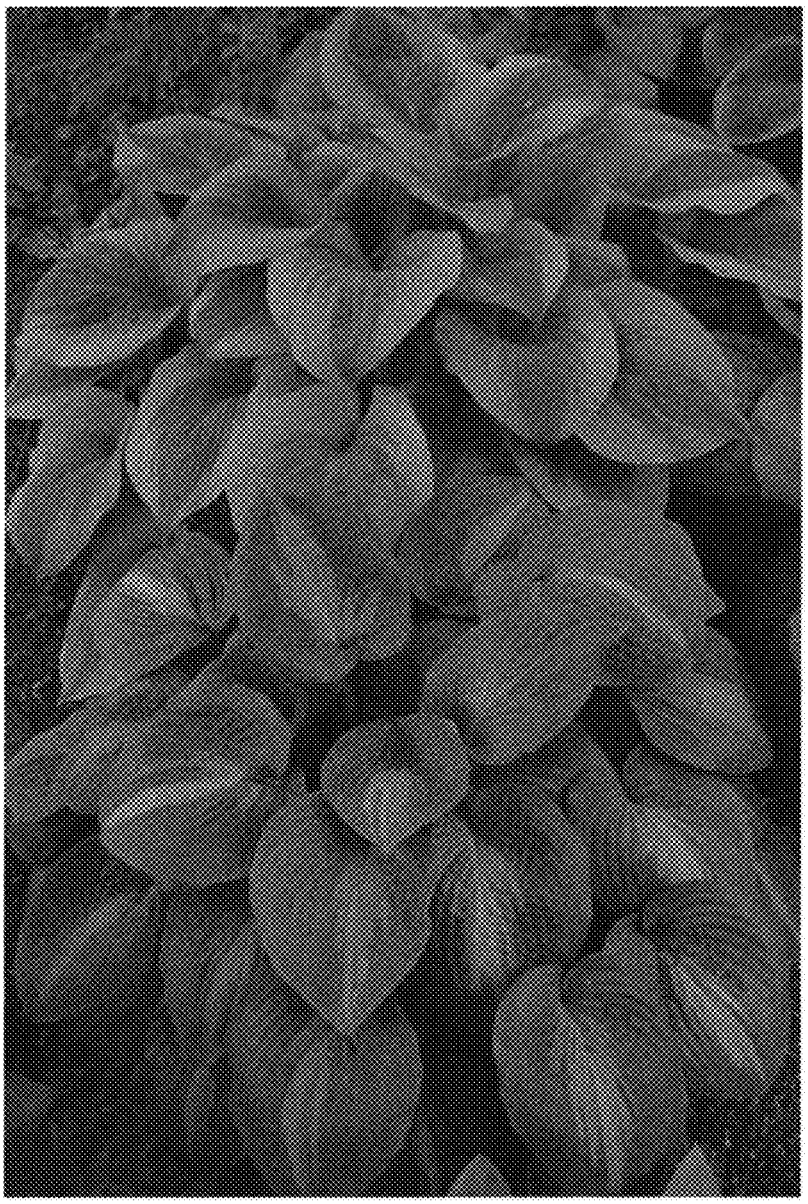
FIG. 4 shows a comparison of the sport parent 'St Paul' (below) and the new plant (above) prior to flowering and growing in a display garden at a nursery in Indianapolis, Ind..
Figure 5:
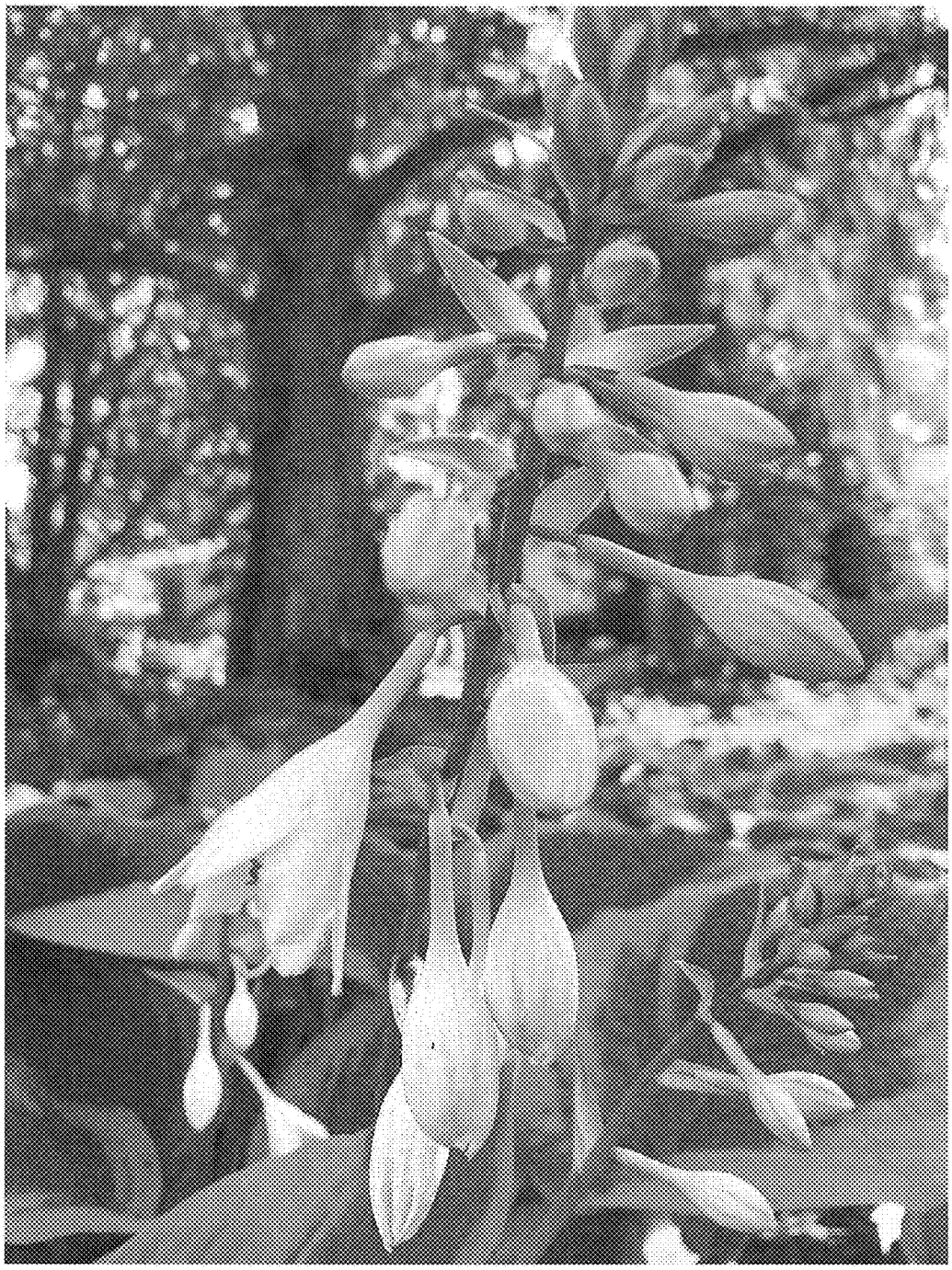
FIG. 5 shows the flowering scape of 'Twin Cities' with open flowers and buds.
Figure 6:
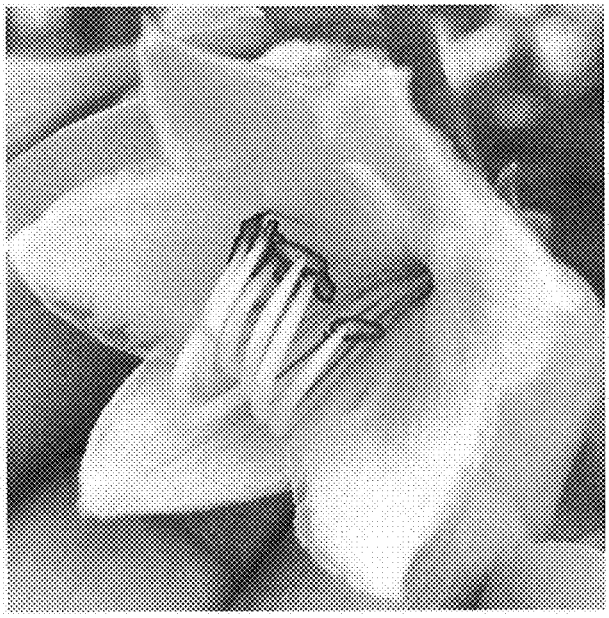
FIG. 6 shows a close-up of the inside of an open flower.
Figure 7:
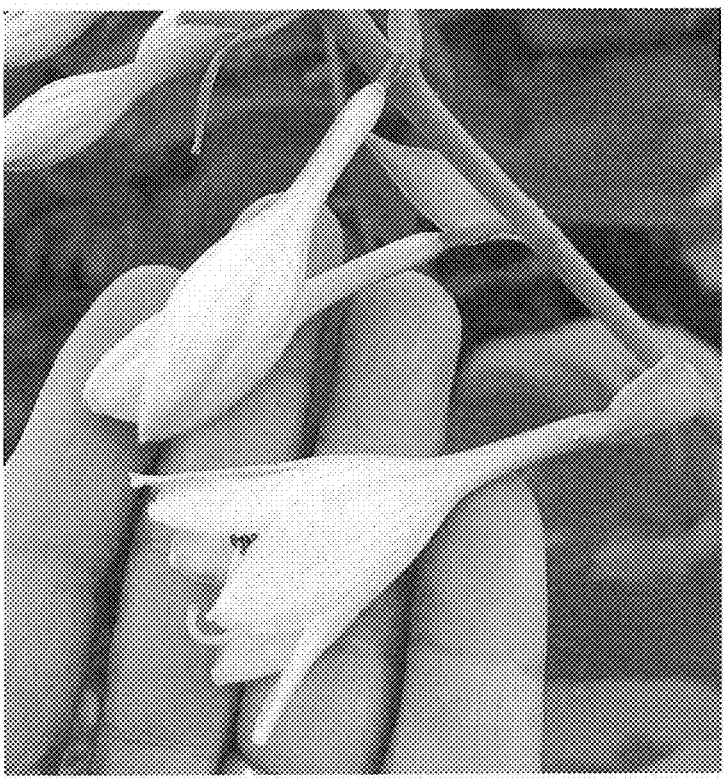
FIG. 7 shows a close-up of the outside of an open flower and buds.

The following descriptions and color references are based on the 2015 edition of The Royal Horticultural Society Colour Chart except where common dictionary terms are used. The new plant, *Hosta* 'Twin Cities', has not been observed under all possible environmental conditions. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of an eight-year-old plant in a shaded display garden in Indianapolis, Ind. provided with supplemental water and fertilizer.

Botanical classification: *Hosta* x hybrid;

Parentage: A partial plant sport mutation of 'St Paul';

Propagation: Garden division and sterile shoot tip plant tissue culture;

Time to initiate roots from tissue culture: About two to three weeks;

Growth rate: Moderately vigorous;

Crop time: About three months to four months to finish during the spring in a one-liter container from rooted tissue culture plantlet;

Rooting habit: Fleshy, lightly branching;

Root color: Typically between RHS 155D and RHS NN155C when actively growing depending on soil mineralization;

Plant shape and habit: Hardy herbaceous perennial with a basal rosette of leaves and petioles emerging from rhizomes producing a low spreading mound with slightly arching scapes flowering just above foliage;

Plant size: Foliage height to about 81.0 cm above soil line to the top of the leaves, and to about 163 cm wide at the widest point about 20.0 cm above the soil line;

Foliage description: Ovate to rounded; acute apex; cordate base; entire margin; glabrous and glaucous both surfaces; blades stiff, bullate, flat to slightly sinuate; moderately impressed adaxial veins and costate, smooth, abaxial veins;

Leaf blade size: To about 33.0 cm long and about 25.5 cm wide; average about 31.5 cm long and 24.0 cm wide; margin variable in an individual leaf and increasing with plant maturity from 1.5 cm to about 5.0 cm wide; center variable in an individual leaf and decreasing with maturity to about 28.0 cm;

Leaf blade color: Early season and expanding adaxial margin between RHS 146D and RHS 145A, center nearest RHS 137B and intermediate melded zone nearest RHS 146B; early season and expanding abaxial margin between RHS 146D and RHS 145A, center nearest RHS 146A and intermediate melded zone nearest RHS 146C; mid-season and later adaxial margins variable, nearest RHS 160A and between RHS 146D and RHS N144A, center nearest RHS 137B and intermediate melded zone variable, between RHS 145A and RHS 146D and between RHS 146C and RHS 138B; mid-season and later abaxial margin variable, nearest RHS N138C and between RHS 11C and RHS 151D, abaxial center nearest RHS N138C, abaxial intermediate zone variable, between RHS N138C and RHS 151D and between RHS 151D and RHS 146D;

Petiole: Glabrous and glaucous both adaxial and abaxial; deeply "V" shaped; stiff; to 53.3 cm long and 22.0 mm wide at base and about 7.0 mm deep near base, average about 48.0 cm long and 18.0 mm wide;

Petiole color: Adaxial margin between RHS 146D and RHS, center between RHS 138A and RHS 137C; abaxial margins nearest RHS 145A center nearest RHS 137C and midrib nearest RHS 145D;

Veins: To seventeen pairs on either side of midrib; parallel; moderately impressed adaxial; costate and smooth abaxial;

Veins color: Adaxial nearest RHS 160A; abaxial nearest RHS 194B;

Flower description:

Buds one to two days prior to opening: Clavate with rounded apex, and narrow tube base; to about 4.7 cm long and 13 mm dimeter at widest bulb portion, with base narrowing in basal 1.8 cm to about 0.3 cm diameter; "bulb portion" is used here to describe the distal inflated portion of the bud that is attached to the pedicel by the narrow tube;

Bud color: Between RHS 85C and RHS 85D distally about one day prior to opening and nearest RHS 85C proximally in tube;

Flowers: Perfect; campanulate; outwardly to slightly drooping; to 5.4 cm long to exserted stigma; corolla fused in basal 3.7 cm, free in the distal 1.5 cm, about 3.6 cm wide at tepal apices, corolla length about 5.2 cm, corolla tube portion to about 2.3 cm long and 0.3 cm diameter; swollen bud portion to size decreasing distally; effective for a normal period, usually about one day on plant; flowers tightly arranged on scape; dropping shortly after opening;

Flowering period: Scapes remain effective with flowers beginning late June for about four weeks;

Inflorescence: With about 40 flowers per scape; flowering in upper 20 cm; mostly secund;

Fragrance: No detectable fragrance;

Tepal: Two nearly identical sets of three, glabrous; entire margins;

*Inner set.*—Average about 4.5 cm long and 9.0 mm wide slightly above fusion point; fused in basal 3.0 cm; clavate with acute apex; entire margin; basal 2.3 cm fused into tube.

*Inner set color.*—Distal portion adaxial center between RHS 85C and RHS 85D and margin nearest RHS NN155D, abaxial between RHS 85D and RHS NN155D; corolla tube portion adaxial nearest RHS NN155D and abaxial nearest RHS 85D.

*Inner set.*—About 4.0 cm long and 8.0 mm wide slightly above fusion point; fused in basal 3.0 cm; clavate with acute apex; entire margin; basal 1.8 cm fused into tube; with an irregular translucent edge of about 1.0 mm wide.

*Inner set color.*—Adaxial and abaxial nearest RHS NN155D with adaxial having very lightly blushed nearest RHS 91D and the center veins nearest RHS 84C; corolla tube base adaxial and abaxial nearest RHS 91D.

Gynoecium: single; to about 5.4 cm long; superior; exerted;

*Style.*—Cylindrical; to about 4.6 cm long, 0.2 cm diameter; arcuate upward 90 degrees in distal 1.2 cm; color nearest RHS 157D distally and nearest RHS 145C proximally.

*Stigma: puberulent; globose; about* 1.2 mm across and 1.0 mm tall; color nearest RHS NN155A.

*Ovary.*—Ellipsoidal; superior; apex rounded; base rounded to truncate; to about 6 mm long and 3 mm diameter in middle; color nearest RHS 145A.

Androecium: Six;

*Filaments.*—Six, approximately 4.7 cm long and 0.1 cm in diameter; curved upward to nearly 90 degrees in the distal 0.8 mm; color distally nearest RHS NN155B, base nearest RHS 145C.

*Anthers.*—Ellipsoidal with rounded ends; dorsifixed; longitudinal; about 3.5 mm long and 1.5 mm wide; color nearest RHS 79A.

*Pollen.*—Spherical; less than 0.1 mm diameter; color nearest RHS 11A.

Peduncle: Cylindrical; usually one per mature division; about 14 per plant; glabrous; glaucous; mostly erect with slightly arching distally; to about 152 cm tall, and about 0.9 cm in diameter at base, average about 145 cm tall and 0.8 cm diameter at base;

Inflorescence: Flowering in distal 22.0 cm of peduncle, to about 9.0 cm wide; with small floral bracts subtending each flower;

Peduncle color: Proximal portion below leaves nearest RHS NN137C, distal portion between RHS N138A and RHS 137A with light blush of nearest RHS 79A;

Pedicel: Terete; glabrous; slightly lustrous; about 1.1 cm long and 0.2 cm diameter decreasing distally; slightly drooping;

Pedicel color: Nearest RHS 193B with light blush of nearest RHS 79D;

Floral bracts: Each flower normally subtended by a single bract; lanceolate; narrowly acute apex and truncate base; entire margin; glabrous and glaucous abaxial and adaxial; persistent through flower drop; to about 4.8 cm long and 1.0 cm wide, decreasing distally; forming upright beak prior to bud development;

Foliar bract color: Adaxial and abaxial between RHS N148B and RHS 146D;

Fruit: Tri-valved dehiscent capsule; oblong, cylindrical; apex acute; base rounded; about 32.0 mm long and 7.0 mm diameter;

Capsule color: Nearest RHS 137B as developing, nearest RHS 161C as seeds dehisce;

Seed: Under natural pollination typically about 30 per capsule; endospermic; flattened-ellipsoidal wing surrounding embryo toward one end; about 6.0 mm long, 3.0 mm wide and 1.0 mm thick at embryo;

Seed color: Nearest RHS 202A;

Disease resistance: The new plant shows some resistance to slug feeding. Other resistance or susceptibility to pests (including: *Odocoileus virginianus* and *Oryctotagus cuniculus*) and diseases common to *Hostas* has not been observed.

Growth: The plant grows best and shows best coloration with good drainage, plenty of water, light cool shade, but is able to tolerate some drought when mature.

Hardiness: The new plant is winter hardy to at least from USDA zone 3 through 8.

It is claimed:

1. A new and distinct *Hosta* plant named 'Twin Cities' as herein described and illustrated.

* * * * *